United States Patent [19]
Manos et al.

[11] Patent Number: 5,283,171
[45] Date of Patent: Feb. 1, 1994

[54] COMPOSITIONS FOR AND DETECTION OF HUMAN PAPILLOMAVIRUS BY SPECIFIC OLIGONUCLEOTIDE POLYMERASE PRIMERS USING THE POLYMERASE CHAIN REACTION

[75] Inventors: M. Michele Manos, Oakland; Deann K. Wright, San Francisco; Yi Ting, Berkeley, all of Calif.; Thomas R. Broker, Rochester, N.Y.; Steven M. Wolinsky, Glencoe, Ill.

[73] Assignees: Hoffmann-La Roche Inc., Nutley, N.J.; The University of Rochester, New York

[21] Appl. No.: 651,356

[22] PCT Filed: Aug. 29, 1989

Related U.S. Application Data

[86] PCT No.: PCT/US89/03747
§ 371 Date: Feb. 5, 1991
§ 102(e) Date: Feb. 5, 1991

[63] Continuation-in-part of Ser. No. 322,550, Mar. 10, 1989, abandoned, which is a continuation-in-part of Ser. No. 243,486, Sep. 9, 1988, abandoned.

[51] Int. Cl.$^5$ .............. C12Q 1/68; C07H 21/04; G01N 33/50
[52] U.S. Cl. ........................ 435/5; 435/6; 435/810; 436/501; 436/811; 536/23.1; 536/24.3; 536/24.31; 536/24.32; 536/34.33; 935/3; 935/20; 935/77; 935/78; 935/88
[58] Field of Search ............ 435/5, 6, 810, 91; 436/501, 811; 536/27, 23.1, 24.3, 24.31–24.33; 935/3, 20, 77, 78, 88

[56] References Cited

U.S. PATENT DOCUMENTS

| | | | |
|---|---|---|---|
| 4,849,331 | 7/1989 | Lorinez | 435/5 |
| 4,849,332 | 7/1989 | Lorinez | 435/5 |
| 4,849,334 | 7/1989 | Lorinez | 435/5 |
| 4,908,306 | 3/1990 | Lorincz | 435/5 |
| 4,983,728 | 1/1991 | Herzog et al. | 536/27 |
| 5,057,411 | 10/1991 | Lancaster et al. | 435/6 |

FOREIGN PATENT DOCUMENTS

| | | |
|---|---|---|
| 0425995 | 5/1991 | European Pat. Off. |
| 8605816 | 10/1986 | PCT Int'l Appl. |
| 8806634 | 9/1988 | PCT Int'l Appl. |
| 8902934 | 4/1989 | PCT Int'l Appl. |
| 8909940 | 10/1989 | PCT Int'l Appl. |

OTHER PUBLICATIONS

Shibata et al. (1988) J. Eup. Med. vol. 167, pp. 225–230.
Schwarz et al. (1983) EMBO j., vol. 2, No. 12, pp. 2341–2348.
Seedorf et al. (1985) Virology, vol. 145, 181–185.
Dartman et al. (1986) Virology, vol. 151, pp. 124–130.
Cole et al. (1987) J. Mol. Biol, vol. 193, pp. 599–608.
Cole et al. (1986) J. of Virology, vol. 58, No. 3, pp. 991–995.
Campione-Piccardo et al., "Type-Specific Identification of HPV Associated with Genital Lesions After Group-Specific Sequence Amplification," Seventh International Papillomavirus Workshop. (1988).
Cornelissen et al., "Detection of HPV DNA by PCR," Seventh International Papillomavirus Workshop (1988).

(List continued on next page.)

Primary Examiner—Margaret Parr
Assistant Examiner—Ardin H. Marschel
Attorney, Agent, or Firm—George M. Gould; Dennis P. Tramaloni; Stacey R. Sias

[57] ABSTRACT

The presence of human papillomavirus (HPV) in a sample can be detected and the HPV typed by a method that involves the amplification of HPV DNA sequences by the polymerase chain reaction (PCR). The primers used in the method are consensus primers that can be used to amplify a particular region of the genome of any HPV. The presence of HPV in a sample is indicated by the formation of amplified DNA. The HPV is typed by the use of type-specific DNA probes specific for the amplified region of DNA.

6 Claims, No Drawings

OTHER PUBLICATIONS

Evander et al., "Specific Amplification of HPV DNA from Clinical Specimens," Seventh International Papillomavirus Workshop. (1988).

Kasher et al., "Alterations in the HPV 6 LCR Generated During Propagation in E. coli and Determination of Authentic Sequences by Genomic Amplification." Seventh International Papillomavirus Workshop. (1988).

Kashima et al., "HPV-DNA in Oral Squamous Cell Carcinoma and Oral Leukoplakia," Seventh International Papillomavirus Workshop. (1988).

Maitland et al., "Human Papillomavirus in Biopsies of Oral Tissue," Seventh International Papillomavirus Workshop. (1988).

Melchers et al., "Diagnosis of HPV Infections in Cervical Scrapes," Seventh International Papillomavirus Workshop. (1988).

Rotenberg et al., "Generation of HPV-11 E1^E4 and E1^E2 cDNAs Through the Use of a Retroviral Vector," Seventh International Papillomavirus Workshop. (1988).

Shah et al., "Papillomavirus Types and Progression of Carceinoma in situ of the Cervix to Invasive Cancer," Seventh International Papillomavirus Workshop. (1988).

Smith et al., "Comparison of HPV Screening Tests for Early Detection of Genital Cancers," Seventh International Papillomavirus Workshop. (1988).

Young et al., "Detection of HPV in Cervical Smear Cells Using PCR," Seventh International Papillomavirus Workshop. (1988).

Goldsborough et al., 1989, Virology 171:306-311.

Maitland et al., 1989, Br. J. Cancer 59:698-703.

McDonnell et al., 1989, N. Engl. J. Med. 320(22):1442-1446.

Melchers et al., 1989, J. Clin. Microb. 27(8):1711-1714.

Roman and Fife, 1989, Clin. Microbiol. Rev. 2(2):166-190.

Tidy et al., Jun. 3, 1989, Lancet 1(8649):1225-1227.

van den Brule et al., 1989, J. Med. Virol. 29:20-27.

Resnick et al., 1990, JNCI 82(18):1477-1484.

Shibata, 1987, Am. J. Clin. Path. 88:524.

1989, Lancet 8646(1):1051-1052.

COMPOSITIONS FOR AND DETECTION OF HUMAN PAPILLOMAVIRUS BY SPECIFIC OLIGONUCLEOTIDE POLYMERASE PRIMERS USING THE POLYMERASE CHAIN REACTION

CROSS-REFERENCE TO RELATED APPLICATIONS

This application is a continuation-in-part of Ser. No. 07/322,550, filed Mar. 10, 1989, now abandoned, which is a continuation-in-part of U.S. patent application Ser. No. 07/243,486 filed on Sep. 9, 1988, now abandoned.

The present invention provides medical research and diagnostic methods for detecting and typing HPV. The method utilizes PCR, a DNA amplification technique widely used in the fields of molecular biology and genetic engineering. The method can also be used to generate information concerning previously unknown strains of HPV and consequently has applications in the field of virology.

Papillomaviruses have been linked to widespread, serious human diseases, especially carcinomas of the genital and oral mucosa. And although genital HPV infection is associated with cancer primarily in women, recent evidence suggests that HPV may play a role in the development of prostate cancer in men. Broker et al., 1986, Cancer Cells 4:17–36, review the molecular, cellular, and clinical aspects of the papillomaviruses and the relationship of HPVs to cancer. HPV types 6, 11, 16, 18, and 33 are known genital HPV types in the human population, and Broker et al., 1986, Cancer Cells 4:589–594, disclose that HPV types 6, 11, 16, 18, and 33 share significant homology at the DNA level, particularly at the L1 open reading frame.

Identification and typing of HPV is quite important, because different types of HPV pose different risks to the affected individuals. For instance, HPV16 and HPV18 have been more consistently identified in higher grades of cervical dysplasia and carcinoma than other HPV types. Webb et al., December 1987, J. Inf. Disease 156(6):912–919, report a method for detecting HPV DNA types that utilizes a reverse-blotting procedure. The procedure involved forming a membrane to which genomic DNA from four different HPV types was bound and then hybridizing labelled DNA from a biological sample to the DNA bound to the membrane. Caussey et al., February 1988, J. Clin. Microbiol, 26(2):236–243 describe similar HPV detection methods.

Shibata et al., January 1988, J. Exp. Med, 167:225–230, disclose the use of PCR to amplify and detect the presence of HPV16 and HPV18 DNA. U.S. Pat. Nos. 4,683,195 and 4,683,202 disclose PCR and the use of PCR to detect the presence or absence of nucleic acid sequence in a sample. European Patent Publication Nos. 229,701 and 269,445 disclose the use of PCR to amplify and detect DNA sequences associated with a wide variety of viruses, including the AIDS virus, HTLV I, and HTLV II.

Maitland et al., May 1988, Seventh International Papillomavirus Workshop, Abstract, p. 5, report the use of PCR to detect HPV16 in oral and cervical biopsies. In addition, Campione-Piccardo et al., May 1988, Seventh International Papillomavirus Workshop, Abstract, p. 19, report the use of a mixture of primers for the specific amplification by PCR of HPV sequences in types 1a, 5, 6a, 8, 11, 16, 18, and 33. A number of other researchers disclosed the use of PCR to amplify and detect HPV sequences at the Seventh International Papillomavirus Workshop.

Despite the use of PCR to amplify and detect HPV sequences, there still remains a need for a simple and rapid method for both detecting and typing HPV in a biological sample. The present invention provides a method that meets that need.

The present invention provides a method for detecting and typing HPV in a sample. The method comprises amplifying a sequence of HPV DNA present in the sample, determining if amplification has occurred, and then hybridizing an HPV type-specific probe to the amplified DNA. The invention also provides novel primers and probes for use in the method.

The present invention provides a method for detecting HPV in a sample, and typing the HPV if present, the method comprising:

(a) treating the sample with consensus HPV primers, an agent for polymerization, and deoxynucleoside 5'-triphosphates under conditions such that an extension product of a consensus primer can be synthesized, wherein said consensus primers are a mixture of oligonucleotides that comprises at least a pair of primers sufficiently complementary to separate single strands of HPV DNA to hybridize thereto so that the extension product synthesized from one member of said pair, when separated from its complementary strand, can serve as a template for synthesis of the extension product of the other member of said pair;

(b) separating the primer extension products, if present, from the templates on which the extension products were synthesized to form single-stranded molecules;

(c) treating the single-stranded molecules generated in step (b), if any, with the consensus primers of step (a) under conditions such that a primer extension product is synthesized using each of the single-stranded molecules produced in step (b) as a template;

(d) repeating steps (b) and (c) at least once;

(e) determining if amplification has occurred; and if amplification has occurred, (f) hybridizing an HPV type-specific DNA probe to said amplified DNA; and (g) determining if hybridization has occurred.

The first step in the method of the invention requires the use of consensus primer pairs that will amplify a discrete region of DNA from HPV DNA present in a sample. These consensus primer pairs are oligonucleotides, and the consensus primers are mixtures of primer pairs. The mixtures used in the method assure that, regardless of the type of HPV present in a sample, HPV DNA corresponding to the region between the "consensus" sequences will be amplified. The PCR products generated from the consensus primers, if HPV is present in the sample, are then analyzed by hybridization with type-specific probes to determine the HPV types present.

Amplification of DNA by the polymerase chain reaction (PCR) is disclosed in U.S. Pat. Nos. 4,683,202 and 4,683,195 and in the related applications noted and incorporated by reference in the Cross-Reference, above. PCR amplification of DNA involves repeated cycles of heat-denaturing the DNA, annealing two oligonucleotide primers to sequences that flank the DNA segment to be amplified, and extending the annealed primers with DNA polymerase. The primers hybridize to opposite strands of the target sequence and are oriented so DNA synthesis by the polymerase proceeds across the region between the primers, effectively doubling the amount of that DNA segment. Moreover, because the extension products are also complementary to and capable of binding primers, each successive cycle essentially doubles the amount of DNA synthesized in the previous cycle. This results in the exponential accumulation of the specific target fragment, at a rate of approximately 2 n per cycle, where n is the number of cycles.

The choice of primers for use in PCR determines the specificity of the amplification reaction. In the amplification steps of the method of the present invention, "consensus" primers are used that will amplify genital HPV sequences present in a sample, regardless of type. The consensus primers of the invention can include degenerate primers, mixtures of the oligonucleotides synthesized so that any one of several nucleotides can be incorporated into a primer at a selected position during synthesis. The consensus primers are sufficiently complementary to all types of HPVs to amplify a DNA sequence of any HPV present in the sample. The consensus primers are also designed to amplify a region of DNA that contains sequences that are specific to each major viral type, so the amplified DNA can therefore be used to type the HPV present in the sample.

The invention, although applicable to any HPV, is exemplified below with reference to genital HPV strains. Furthermore, the primers and probes of the invention can be targeted to areas of the HPV genome other than those described below, provided that the particular area targeted can be amplified using consensus primers and the amplified DNA can be typed using type-specific probes.

The first step of the method of the present invention involves the amplification of an HPV sequence, if that sequence is present in a sample, by PCR using consensus primers. Illustrative consensus primers of the invention are referred to by the region of the HPV genome the primers are used to amplify. The HPV genome is circular. The genome of genital HPVs is oriented as follows: E6, E7, E1, E2, E4, E5a, E5b, L2, L1, and URR. "E" and "L" designations indicate open reading frames, but many of the open reading frames overlap. For instance, E4 is totally contained within the E2 open reading frame. URR is the transcriptional regulatory region. Primers can be used to amplify a sequence that spans one or more regions of the HPV genome.

For instance, the L1/E6 consensus primer combinations of the invention are designed to amplify a sequence of DNA from any genital HPV. The amplified sequence extends from L1 across the URR and into E6 and thus contains portions of the L1 and E6 regions with the URR region sandwiched in between the L1 and E6 regions. Thus, the consensus primer pairs consist of a first primer specific for a sequence in the L1 region and a second primer specific for a sequence in the E6 region. As shown in Table 1, below, the first L1-specific primer can be either FS10, FS17, or MY01, while the second, E6-specific primer is at least a 1:1 mixture of JS15 and JS16, although the mixture can also contain more JS15 than JS16. Table 1 also depicts the sequence each primer and the corresponding sequence (and nucleotide position of that sequence) as it occurs in the genomes of several well-known genital HPVs (Types 6, 11, 16, 18, and 33). A dash in a sequence indicates that the genomic sequence is identical to the primer sequence. Nucleotides are abbreviated as follows:

| Symbol | Meaning | Origin |
|---|---|---|
| G | G | Guanine |
| A | A | Adenine |
| T | T | Thymine |
| C | C | Cytosine |
| R | G or A | puRine |
| Y | T or C | pYrimidine |
| M | A or C | aMino |
| K | G or T | Keto |
| S | G or C | Strong interaction (3 H bonds) |
| W | A or T | Weak interaction (2 H bonds) |
| H | A or C or T | not-G, H follows G in the alphabet |
| B | G or T or C | not-A, B follows A |
| V | G or C or A | not-T (not-U), V follows U |
| D | G or A or T | not-C, D follows C |
| N | G or A or T or C | aNy |

TABLE 1

L1/E6 Consensus Primers and Amplification Products

L1 Consensus Positive Strand Primers

| | | | | | | | | | | | | | | | | | | | | | | | | | | | | |
|---|---|---|---|---|---|---|---|---|---|---|---|---|---|---|---|---|---|---|---|---|---|---|---|---|---|---|---|---|
| FS10 | 25mer | 5' | C | T | G | T | G | G | T | A | G | A | T | A | C | C | A | C | A | C | G | C | A | G | T | A | C |
| HPV06 | 6770 | | — | — | — | — | — | — | — | — | — | — | — | — | — | — | — | — | — | — | — | — | — | — | — | — | — |
| HPV11 | 6756 | | — | — | — | — | — | — | — | — | — | — | — | — | — | — | — | — | — | — | — | — | — | — | — | — | — |
| HPV16 | 6633 | | — | — | — | — | T | — | — | T | — | — | — | — | — | — | T | — | — | — | — | — | — | — | — | — | — |
| HPV18 | 6587 | | — | — | — | — | — | — | — | — | — | — | — | — | — | — | — | — | — | T | — | — | — | — | — | — | — |
| HPV33 | 6587 | | — | — | — | — | — | — | — | — | — | — | — | — | — | — | — | — | — | T | — | — | — | — | — | — | — |
| FS17 | 20mer | 5' | G | A | T | C | A | G | T | T | T | C | C | Y | Y | T | K | G | G | A | C | G | | | | | |
| MY01 | 20mer | 5' | G | A | T | C | A | G | T | W | T | C | C | Y | Y | T | K | G | G | A | C | G | | | | | |
| HPV06 | 7151 | | — | — | — | — | — | — | — | A | — | — | — | T | T | — | G | — | — | — | — | — | | | | | |
| HPV11 | 7136 | | — | — | — | — | — | — | — | T | — | — | — | C | C | — | T | — | — | — | — | — | | | | | |
| HPV16 | 7015 | | — | — | — | — | — | — | — | T | — | — | — | T | T | — | A | — | — | — | — | — | | | | | |
| HPV18 | 6993 | | — | — | — | — | — | A | — | A | — | — | — | C | C | — | T | — | — | — | — | — | | | | | |
| HPV33 | 6968 | | — | — | — | — | — | — | — | T | — | — | — | T | T | — | G | — | — | — | — | — | | | | | |

URR/E6 Consensus Negative Strand Primer

| | | | | | | | | | | | | | | | | | | | | |
|---|---|---|---|---|---|---|---|---|---|---|---|---|---|---|---|---|---|---|---|---|
| JS15 | 18mer | 5' | C | C | G | T | T | T | T | C | G | G | T | T | S | A | A | C | C | G |
| HPV06 | 60 | | — | — | — | — | — | — | — | — | — | — | — | — | G | — | — | — | — | — |
| HPV11 | 60 | | — | — | — | — | — | — | — | — | — | — | — | — | G | — | — | — | — | — |
| HPV16 | 60 | | — | — | — | G | — | — | — | — | — | — | — | — | C | — | — | — | — | — |
| HPV33 | 64 | | — | — | — | — | — | — | — | — | — | — | — | — | G | — | — | — | — | — |
| JS16 | 19mer | 5' | C | C | G | T | T | T | T | C | G | G | T | C | C | C | G | A | C | C | G |
| HPV18 | 68 | | — | — | — | — | — | — | — | — | — | — | — | — | — | — | — | — | — | — | — |

Predicted Sizes Of PCR Products

| | | |
|---|---|---|
| + PRIMER | FS10 | FS17 or MY01 |
| − PRIMER | JS15 and JS16 | JS15 and JS16 |
| HPV06 | 1192 bp | 822 bp |
| HPV11 | 1235 bp | 856 bp |
| HPV16 | 1387 bp | 958 bp |
| HPV18 | 1367 bp | 932 bp |

TABLE 1-continued

| L1/E6 Consensus Primers and Amplification Products | | |
|---|---|---|
| HPV33 | 1434 bp | 1005 bp |

As shown in Table 1, FS10 is a 25-mer that has 3 mismatches with HPV16 and 1 mismatch with HPV18 and HPV33. FS17 is a degenerate primer with 1 or 2 mismatches to different HPVs. MY01 is similar to FS17, contains 1 more degenerate base to decrease mismatches and to potentially cover a wider range of HPVs. JS15 is a degenerate 18-mer for the negative strand in E6 of HPVs 6, 11, 16, and 33, whereas JS16 is a 19-mer serving the same function for HPV18.

Once a sample has been treated with the L1/E6 primers shown above under conditions suitable for PCR, the method of the invention requires the determination of whether amplification has occurred. If amplification has occurred with the L1/E6 primers, HPV sequences are present in the sample. The use of an internal amplification control to assure the competency of a sample for PCR is within the scope of the invention and reduces the likelihood of false negative results. There are a variety of ways to determine whether amplification has occurred. A portion of the reaction mixture can be subjected to gel electrophoresis and the resulting gel stained with ethidium bromide and exposed to ultraviolet light to observe whether a product of the expected size is present. Labeled primers or deoxyribonucleotide 5'-triphosphates can be added to the PCR reaction mixture, and incorporation of the label into the amplified DNA is measured to determine if amplification occurred. Another method for determining if amplification has occurred is to test a portion of PCR reaction mixture for ability to hybridize to a labeled oligonucleotide probe designed to hybridize to only the amplified DNA. The probe must be a consensus probe so that amplified DNA from any HPV can be detected. For instance, amplification of HPV DNA using the L1/E6 consensus primers FS10, JS15, and JS16 can be detected using the L1/E6 consensus primer FS17 or MY01. Alternatively, the determination of amplification and identification of HPV type can be carried out in one step by testing a portion of the PCR reaction mixture for its ability to hybridize to one or more type-specific probes.

An important aspect of the present invention relates to the novel probes provided for use in the present methods. Whether these probes are consensus probes for determining if amplification has occurred or whether these probes are type-specific probes, the probes can be used in a variety of different hybridization formats. Although solution hybridization of a nucleic acid probe to a complementary target sequence is clearly within the scope of the present invention, commercialization of the invention will likely result in the use of immobilized probes and thus a quasi "solid-phase" hybridization. In this format, the probe is covelently attached to a solid support and then the target sequences are then hybridized with the probe. In this method, the probes are attached to a solid support by virtue of long stretches of T residues; these T residues are added to the probe during synthesis of the probe on an automated synthesizer after the hybridizing sequence is synthesized. A variety of dyes and chromogens and corresponding labels are available for nucleic acid detection systems.

The present invention has led and will continue to lead to the discovery of so many previously unknown (or at least uncharacterized) HPV types, however, that the embodiment of the invention in which consensus probes are used to determine if amplification has occurred will continue to decline in importance. This is because that with each new type of HPV discovered there comes a corresponding need to make the consensus probe more generic to ensure that the new type will be detected. To overcome this problem, the present invention provides a new type of consensus probe. This new type of probe essentially consists of a sequence of DNA from one or more HPV viruses that comprises all or most of the DNA sequence that lies between the two sequences on the HPV genome corresponding to the primers used in the amplification. The consensus probe should not, however, comprise a sequence complementary to either primer used to amplify the HPV DNA in the sample. This new type of consensus probe has greater versatility in that it has more sequence available for hybridization than the other consensus probes of the invention. In addition, the consensus probe can be generated with PCR with primers that hybridize to sequences that lie inside the region of DNA defined by the primers used to amplify the HPV DNA sequences present in a sample.

The present invention provides a number of type-specific probes for use with the L1/E6 consensus primers of the invention. These probes are set forth in Table 2, below. Those skilled in the art will recognize that although the specific primers and probes of the invention exemplified herein have a defined number of nucleotide residues, one or more nucleotide residues may be added or deleted from a given primer or probe typically without great impact on the suitability of that primer or probe in the present methods.

TABLE 2

| HPV Typing Probes For Use with L1/L6 Consensus Primers | | | |
|---|---|---|---|
| Specificity | Sequence | Size | Designation |
| HPV6 | 5'CCAAACAGTAAGAGC | (15-mer) | FS18 |
| HPV11 | 5'GGCTGTAGAGGGCTTAGAC | (19-mer) | FS19 |
| HPV16 | 5'GGTTGAAGCTACAAAATGGGCC | (22-mer) | JS17 |
| HPV18 | 5'GTAGCGCACCTGGACAGG | (18-mer) | FS21 |
| HPV33 | 5'CAGGTAGTGACTCAC | (15-mer) | FS22 |

FS19 and JS17 can specifically detect HPV11 and HPV16, respectively. FS18 shows some hybridization with the HPV11 PCR product. UWGCG GAP program analysis comparing FS18 sequence and HPV11 sequence indicates a 73% homology of FS18 to HPV11 in the amplified region. The cross-hybridization could be minimized by increasing the stringency of washing. FS21 was specific for HPV18.

The L1/E6 primers disclosed above provide for the amplification of relatively large segments of HPV DNA. However, use of primers that result in shorter PCR products can have several advantages, including reduced extension and denaturation time and decreased denaturation temperature. The L1 consensus primers of the invention are illustrative of primers of the invention designed to amplify relatively small segments of the HPV genome to achieve such advantages. The L1 consensus primers produce a PCR product corresponding to sequences in the L1 open reading frame and are depicted in Table 3, below.

has occurred simply involves determining whether the label is present on the solid support. This procedure can be varied, however, and works just as well when the target is labeled and the probe is bound to the solid support. Many methods for labelling nucleic acids, whether probe or target, are known in the art and are suitable for purposes of the present invention. In the laboratory work involved in reducing the present invention to practice, probes were typically labeled with radioactive phosphorous $^{32}P$, by treating the probes with polynucleotide kinase in the presence of radiolabelled ATP. For commercial purposes, however,

TABLE 3

L1 Consensus Primers and Amplification Products

L1 Consensus Positive Strand Primer

| | | | | | | | | | | | | | | | | | | | | |
|---|---|---|---|---|---|---|---|---|---|---|---|---|---|---|---|---|---|---|---|---|
| MY11 | 20mer | 5' | G | C | M | C | A | G | G | G | W | C | A | T | A | A | Y | A | A | T | G | G |
| HPV06 | 6722 | | — | — | C | — | — | — | — | — | A | — | — | — | — | — | C | — | — | — | — | — |
| HPV11 | 6707 | | — | — | T | — | — | — | — | — | A | — | — | — | — | — | C | — | — | — | — | — |
| HPV16 | 6582 | | — | — | A | — | — | — | — | — | C | — | — | C | — | — | T | — | — | — | — | — |
| HPV18 | 6558 | | — | — | A | — | — | — | — | — | T | — | — | — | — | — | C | — | — | — | — | — |
| HPV33 | 6539 | | — | — | A | — | — | A | — | — | T | — | — | — | — | — | T | — | — | — | — | — |

L1 Consensus Negative Strand Primer

| | | | | | | | | | | | | | | | | | | | | |
|---|---|---|---|---|---|---|---|---|---|---|---|---|---|---|---|---|---|---|---|---|
| MY09 | 20mer | 5' | C | G | T | C | C | M | A | R | R | G | G | A | W | A | C | T | G | A | T | C |
| HPV06 | 7170 | | — | — | — | — | — | C | — | A | A | — | — | — | T | — | — | — | — | — | — | — |
| HPV11 | 7155 | | — | — | — | — | — | A | — | G | G | — | — | — | A | — | — | — | — | — | — | — |
| HPV16 | 7033 | | — | — | — | — | — | T | — | A | A | — | — | — | A | — | — | — | — | — | — | — |
| HPV18 | 6712 | | — | — | — | — | — | A | — | G | G | — | — | — | T | — | T | — | — | — | — | — |
| HPV33 | 6987 | | — | — | — | — | — | C | — | A | A | — | — | — | A | — | — | — | — | — | — | — |

Predicted sizes of PCR products from the MY11 and MY09 L1 Consensus Primer Pair

HPV06 448 bp
HPV11 448 bp
HPV16 451 bp
HPV18 454 bp
HPV33 448 bp

A preferred embodiment of the method of the present invention for genital HPVs comprises amplification of HPV sequences, if present in the sample, with the L1 consensus primers MY09 and MY11; determination of amplification by hybridization of a portion of the PCR reaction mixture with a generic genital HPV probe; and finally, type determination with type-specific probes. To determine if amplification of HPV DNA sequences has occurred in a sample that has been treated with the L1 consensus primers of the invention, a portion of the PCR reaction mixture can be hybridized with L1 consensus probes, depicted in Table 4.

other non-radioactive labeling systems may be preferred, i.e., horseradish peroxidase-avidin-biotin systems.

Whatever the labeling system used once a determination has been made that the L1 consensus probe has hybridized to amplified DNA present in the sample, the amplified DNA is typed to determine the HPV types present in the sample. Practice of the present invention has led to the discovery of many previously uncharacterized HPV types. For example, three clinical samples examined by the present method contained five different HPV types with sequences markedly different than

TABLE 4

L1 Consensus Probes

| | | | | | | | | | | | | | | | | | | | | | | | |
|---|---|---|---|---|---|---|---|---|---|---|---|---|---|---|---|---|---|---|---|---|---|---|---|
| FS10 | | 5' | C | T | G | T | G | G | T | A | G | A | T | A | C | C | A | C | A | C | G | C | A | G | T | A | C |
| MY18 | | 5' | — | — | — | — | T | — | — | T | — | — | — | — | — | T | — | — | — | — | — | — | — | — | — | — | — |
| MY19 | | 5' | — | — | — | — | — | — | — | — | — | — | — | — | — | — | — | T | — | — | — | — | — | — | — | — | — |

Sequence of HPV types in Region of Consensus Probe

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| HPV6 | 6771 | 5' | C | T | G | T | G | G | T | A | G | A | T | A | C | C | A | C | A | C | G | C | A | G | T | A | C |
| HPV11 | 6756 | 5' | — | — | — | — | — | — | — | — | — | — | — | — | — | — | — | — | — | — | — | — | — | — | — | — | — |
| HPV16 | 6631 | 5' | — | — | — | — | T | — | — | T | — | — | — | — | — | T | — | — | — | — | — | — | — | — | — | — | — |
| HPV18 | 6607 | 5' | — | — | — | — | — | — | — | — | — | — | — | — | — | — | — | T | — | — | — | — | — | — | — | — | — |
| HPV33 | 6588 | 5' | — | — | — | — | — | — | — | — | — | — | — | — | — | — | — | T | — | — | — | — | — | — | — | — | — |
| Isolate | 36 | 5' | — | — | — | — | T | — | — | G | — | — | — | — | — | T | — | — | C | A | — | A | — | — | C | — | — |
| Isolate | 88 | 5' | — | A | — | — | — | — | — | — | — | — | — | — | — | T | — | — | T | — | — | — | — | C | — | — |

When a portion of the PCR reaction mixture contains DNA that hybridizes to a probe contained in the L1 consensus probe mixture, the sample contains HPV DNA. There are a number of ways to determine whether a probe has hybridized to a DNA sequence contained in a sample. Typically, the probe is labeled in a detectable manner, the target DNA (i.e., the amplified DNA in the PCR reaction buffer) is bound to a solid support, and determination of whether hybridization the published sequences for HPVs. These new sequences are an important aspect of the present invention, as are the probes that will hybridize to these sequences in a type-specific fashion. These new sequences are depicted below. Degenerate nucleotides are as defined above and correspond to the degenerate nucleotides in the primers used to amplify the region or to variation within the type.

The DNA Sequence of the L1 Amplified Regions of HPV
Isolates 36A, 36B, 88, 238A, and 238B

Isolate 36A

| | | | | | |
|---|---|---|---|---|---|
| 1 | GCMCAGGGWC | ATAAYAATGG | TATATGTTGG | CACAATCAAT | TGTTTTTAAC |
| 51 | AGTTGTAGAT | ACTACTCGCA | GCACCAATCT | YTCTGTGTGT | GCTTCTACTA |
| 101 | CTTCTCCTAT | TCCTAATGAA | TACACACCTA | CCAGTTTTAA | AGAATATGCC |
| 151 | AGACATGTGG | RGGAATTTGA | TTTGCAGTTT | ATAYTTCAAC | TGTGTAAAAT |
| 201 | AACWTTAACT | ACAGAGGTAA | TGTCATACAT | TCATAATATG | AATACCACTA |
| 251 | TTTTGGAGGA | TTGGAATTTT | GGTRTTACAC | CACCTCCTAC | TGCTARTTTA |
| 301 | GTTGACACAT | ACCGTTTTGT | TCAATCTGCT | GCTGTAACTT | GTCAAAGGA |
| 351 | CACCGCACCG | CCAGTTAAAC | AGGACCCTTA | TGACAAACTA | AAGTTTTGGA |
| 401 | CTGTAAATCT | TAAGGAAAGG | TTTTCTGCAG | ATCTTGATCA | GTWTCCYYTK |
| 451 | GGACG | | | | |

Isolate 36B

| | | | | | |
|---|---|---|---|---|---|
| 1 | GCMCAGGGWC | ATAAYAATGG | TATATGTTGG | GGAAATCAGC | TATTTTTAAC |
| 51 | TGTGGTTGAT | ACTACCCGTA | GTACTAACAT | GACTTTGTGY | GCCACTGCAA |
| 101 | CATCTGGTGA | TACATATACA | GCTGCTAATT | TTAAGGAATA | TTTAAGACAT |
| 151 | GCTGAAGAAT | ATGATGTGCA | ATTTATATTT | CAATTGTGTR | AAATAACATT |
| 201 | AACTGTTGAA | GTTATGTCAT | ATATACACAA | TATGAATCCT | AACATATTAG |
| 251 | AGGAGTGGAA | TGTTGGTGTT | GCACCACCAC | CTTCAGGAAC | TTTAGAAGAT |
| 301 | AGTTATAGGT | ATGTACAATC | AGAAGCTATT | CGCTGTCAGG | CTAAGGTAAC |
| 351 | AACGCCAGAA | AAAAAGGATC | CTTATTCAGA | CTTTTCCTTT | TGGGAGGTAA |
| 401 | ATTTATCTGA | AAAGTTTTCT | ACTGATTTAG | GATCAGTWTC | CYYTKGGACG |

Isolate 88

| | | | | | |
|---|---|---|---|---|---|
| 1 | GCMCAGGGWC | ATAAYAATGG | CATATGCTGG | GGTAATCAGG | TATTTGTTAC |
| 51 | TGTTGTGGAT | ACTACCAGAA | GCACCAACAT | GACTATTAAT | GCAGCTAAAA |
| 101 | GCACATTARC | TAAATATGAT | GCCCGTGAAA | TCAATCAATA | CCTTCGCCAT |
| 151 | GTGGAGGAAT | ATGAACTACA | GTTTGTGTTT | CAACTTTGTA | AAATAACCTT |
| 201 | AACTGCAGAR | GTTATGGCAT | ATTTGCATAA | TATGAATAAT | ACTTTATTRG |
| 251 | ACGATTGGAA | TATTGGCTTA | TCCCCACCAG | TTGCAACTAG | CTTAGAGGAT |
| 301 | AAATATAGGT | ATATTAAAAG | CACAGCTRTT | ACAYGTCAGA | GGGAACAGCC |
| 351 | CCCTGCAGAA | AAGCAGGATC | CCCTGGCTAA | ATATAAGTTT | TGGGAAGTTA |
| 401 | ATTTACAGGA | CAGCTTTTCT | GCAGACCTGG | GATCAGTWTC | CYYTKGGACG |

Isolate 238A

| | | | | | |
|---|---|---|---|---|---|
| 1 | GCMCAGGGWC | ATAAYAATGG | TATTTGTTGG | CATAATCART | TATTTTTAAC |
| 51 | TGTTGTAGAT | ACTACTAGAA | GCACTAATTT | TTCTGTATGT | GTAGGTACAC |
| 101 | AGGCTAGTAG | CTCTACTACA | ACGTATGCCA | ACTCTAATTT | TAAGGAATAT |
| 151 | TTAAGACATG | CAGAAGAGTT | TGATTTACAG | TTTGTTYTTC | AGTTATGTAA |
| 201 | AATTAGTTTA | ACTACTGAGG | TAATGACATA | TATACATTCT | ATGAATTCTA |
| 251 | CTATATTGGA | AGAGTGGAAT | TTTGGTCTTA | CCCCACCACC | GTCAGGTACT |
| 301 | TTAGAGGAAA | CATATAGATA | TGTAACATCA | CAKGCTATTA | GTTGCCAACG |
| 351 | TCCTCAACCT | CCTAAAGAAA | CAGAGGACCC | ATATGCCAAG | CTATCCTTTT |
| 401 | GGGATGTAGA | TCTTAAGGAA | AAGTTTTCTG | CAGAATTAGA | TCAGTWTCCY |
| 451 | YTKGGACG | | | | |

Isolate 238B

| | | | | | |
|---|---|---|---|---|---|
| 1 | GCMCAGGGWC | ATAAYAATGG | TATTTGTTGG | GGCAATCAGT | TATTTGTTAC |
| 51 | TGTGGTAGAT | ACCACACGTA | GTACCAATAT | GTCTGTGTGT | GCTGCAATTG |
| 101 | CAAACAGTGA | TACTACATTT | AAAAGTAGTA | ATTTTAAAGA | GTATTTAAGA |
| 151 | CATGGTGAGG | AATTTGATTT | ACRATTTATA | TTTCAGTTAT | GCAAAATAAC |
| 201 | ATTATCTGCA | GACATAATGA | CATATATTCA | CAGTATGAAT | CCTGCTATTT |
| 251 | TGGAAGATTG | GAATTTTGGA | TTGACCACAC | CTCCCTCAGG | TTCTTTAGAG |
| 301 | GATACCTATA | GGTTTGTAAC | CTCACAGGCC | ATTACATGTC | AAAAARCTGC |
| 351 | CCCCCAAAAG | CCCAAGGAAG | ATCCATTTAA | AGATTATGTA | TTTTGGGAGG |
| 401 | TTAATTTAAA | AGAAAAGTTT | TCTGCAGATT | TAGATCAGTW | TCCYYTKGGA |
| 451 | CG | | | | |

Isolate 155A and 155B

| | | | | | |
|---|---|---|---|---|---|
| 1 | TATATGCTGG | TTTAATCAAT | TGTTTGTCAC | GGTGGTGGAT | ACCACCCGCA |
| 51 | GCACCAATTT | TACTATTAGT | GCTGCTACCA | ACACCGAATC | AGAATATAAA |
| 101 | CCTACCAATT | TTAAGGAATA | CCTAAGACAT | GTGGAGGAAT | ATGATTTGCA |
| 151 | GTTTATATTC | CAGTTGTGTA | AGGTCCGTCT | GACTCCAGAG | GTCATGTCCT |
| 201 | ATTTACATAC | TATGAATGAC | TCCTTATTAG | ATGAGTGGAA | TTTTGGTGTT |
| 251 | GTGCCCCCTC | CCTCCACAAG | TTTAGATGAT | ACCTATAGGT | ACTTGCAGTC |
| 301 | TCGCGCCATT | ACTTGCCAAA | AGGGGGCCGC | CGCCGCCAAG | CCTAAGGAAG |
| 351 | ATCCTTATGC | TGGCATGTCC | TTTTGGGATG | TAGATTTAAA | GGACAAGTTT |
| 401 | TCTACTGATT | TG | | | |

Isolate C14

| | | | | | |
|---|---|---|---|---|---|
| 1 | TATTTGTTGG | CATAATCAGT | TGTTTGTTAC | TGTAGTGGAC | ACTACCCGCA |
| 51 | GTACTAATTT | AACATTATGT | GCCTCTACAC | AAAATCCTGT | GCCAAATACA |
| 101 | TATGATCCTA | CTAAGTTTAA | GCACTATAGT | AGACATGTGG | AGGAATATGA |
| 151 | TTTACAGTTT | ATTTTTCAGT | TGTGCACTAT | TACTTTAACT | GCAGAGGTTA |
| 201 | TGTCATATAT | CCATAGTATG | AATAGTAGTA | TATTGGAAAA | TTGGAATTTT |
| 251 | GGTGTACCTC | CACCACCTAC | TACAAGTTTA | GTGGATACAT | ATCGTTTTGT |
| 301 | GCAATCCGTT | GCTGTTACCT | GTCAAAAGGA | TACTACACCT | CCAGAAAAGC |
| 351 | AGGATCCATA | TGATAAATTA | AAGTTTTGGA | CTGTTGACCT | AAAGGAAAAA |
| 401 | TTTTCCTCCG | ATTTG | | | |

Those skilled in the art will recognize that with the above sequence information, primers and probes for amplifying and detecting these new HPV isolates can be readily obtained. In addition, these sequences enable one to isolate the entire virus from samples containing the virus. Isolate 238B corresponds to the HPV31 type described in the literature. A cervical carcinoma isolate, C14, is a variant of HPV45. The discovery of these new HPV isolates led to the creation of additional L1 con- The present invention provides a number of probes for typing amplified DNA produced from L1 consensus primers. These probes are depicted below in Table 5.

TABLE 5

HPV Typing Probes For Use with L1 Consensus Primers

| Probe | Specificity | Sequence | Genome Position |
|---|---|---|---|
| MY12 | HPV6 | 5'CATCCGTAACTACATCTTCCA | 6813–6833 |
| MY13 | HPV11 | 5'TCTGTGTCTAAATCTGCTACA | 6800–6820 |
| MY14 | HPV16 | 5'CATACACCTCCAGCACCTAA | 6926–6945 |
| WD74 | HPV18 | 5'GGATGCTGCACCGGCTGA | 6905–6922 |
| MY16 | HPV33 | 5'CACACAAGTAACTAGTGACAG | 6628–6648 |
| MY58 | HPV16 | 5'TTGTAACCCAGGCAATTGCT | 6897 |
| MY59 | HPV33 | 5'AAAAACAGTACCTCCAAAGGA | 6877 |
| MY60 | HPV18 | 5'CAGTCTCCTGTACCTGGG | 6657 |
| MY61 | HPV11 | 5'CACACCTGAAAAAGAAAAACAG | 7051 |
| MY62 | HPV6 | 5'CTCCTGAAAAGGAAAAGCCA | 7068 |
| MY63 | HPV6 | 5'TGGCTTTTCCTTTTCAGGAG | 7068 |
| MY64 | HPV33 | 5'TCCTTTGGAGGTACTGTTTTT | 6877 |
| MY65 | HPV11 | 5'CTGTTTTTCTTTTTCAGGTGTG | 7051 |
| WD126 | HPV31 | 5'CCAAAAGCCCAAGGAAGATC | N.D. |
| WD127 | HPV31 | 5'CAAAAGCCCAAGGAAGATC | N.D. |
| WD128 | HPV31 | 5'TTGCAAACAGTGATACTACATT | N.D. |
| MY69 | HPV45 | 5'ATACTACACCTCCAGAAAAGC | N.A. |
| MY70 | HPV45 | 5'TAGTGGACACTACCCGCAG | N.A. |
| WD150 | HPV11 | 5'CAGAAACCCACACCTGAAAAAGA | 7059 |
| WD151 | HPV11 | 5'AGAAACCCACACCTGAAAAAGAA | 7058 |
| WD152 | HPV16 | 5'TTTGTAACCCAGGCAATTGCT | 6898 |
| WD153 | HPV11 | 5'GTTTGTAACCCAGGCAATTGCT | 7053 |

N.D.: Not determined
N.A.: Not available sensus probes for use in conjunction with FS10, MY18, and MY19. These L1 consensus probes are depicted below under the FS10 probe sequence to demonstrate the similarity to the FS10 sequence. L1 consensus probe WD147 will hybridize to HPV45 DNA.

The present invention also provides consensus primers and HPV typing probes for detection of DNA sequences specific for the E6 region of genital HPVs. These probes are particularly preferred, because in some HPV-infected individuals, the HPV genome is

| | | | | | | | | | | | | | | | | | | | | |
|---|---|---|---|---|---|---|---|---|---|---|---|---|---|---|---|---|---|---|---|---|
| FS10 | 5' | C | T | G | T | G | G | T | A | G | A | T | A | C | C | A | C | A | C | G | C | A | G | T | A | C |
| MY66 | | — | A | — | — | T | — | — | — | — | — | — | — | — | — | T | — | — | T | — | — | — | — | C | — | — |
| MY55 | | — | — | — | — | — | — | — | T | — | — | — | — | — | T | — | — | C | — | — | T | — | — | — | — | — |
| MY39 | | — | — | — | — | T | — | — | G | — | — | — | — | — | T | — | — | C | A | — | A | — | — | C | — | — |
| MY56 | | — | — | — | — | T | — | — | — | — | — | — | — | — | T | — | — | T | A | — | A | — | — | C | — | — |
| MY57 | | — | — | — | — | — | — | — | — | — | — | — | — | — | — | — | — | — | T | — | — | — | — | — | — | — |
| WD147 | | — | — | — | — | A | — | — | G | — | — | C | — | — | T | — | — | C | — | — | — | — | — | — | — | — |

As noted above, the diversity of HPV types may mandate the use of longer consensus probes that contain almost all of the amplified sequence except that portion corresponding to the primers used in the amplification step of the present method. This diversity in HPV types also demonstrates the need for the type-specific probes provided by the present invention.

partially deleted or rearranged such that only E6- and E7-related sequences are present. The E6 consensus primer pairs of the invention comprise primer pairs in which one primer is complementary to sequences near the border of the URR and E6 regions and the other primer is complementary to sequences in either the E7 region near the E6-E7 border (the E6 and E7 open reading frames overlap) or in the E6 region. These E6 consensus primers are depicted below in Table 6.

TABLE 6

E6 Consensus Primers

URR/E6 Consensus Positive Strand Primers

| | | | | | | | | | | | | | | | | | | |
|---|---|---|---|---|---|---|---|---|---|---|---|---|---|---|---|---|---|---|
| WD73 | | 5' | C | G | G | T | T | S | A | | A | C | C | G | A | A | A | C | G | G |
| WD72 | | 5' | C | G | G | T | C | G | G | A | C | C | G | A | A | A | A | C | G | G |
| WD76 | | 5' | C | G | G | T | T | S | A | | A | C | C | G | A | A | A | M | C | G | G |
| WD77 | | 5' | C | G | G | T | T | C | A | | A | C | C | G | A | A | A | M | C | G | G |
| HPV06 | 43 | 5' | C | G | G | T | T | C | A | | A | C | C | G | A | A | A | A | C | G | G |
| HPV11 | 43 | | — | — | — | — | — | — | — | | — | — | — | — | — | — | — | — | — | — | — |
| HPV16 | 43 | | — | — | — | — | — | G | — | | — | — | — | — | — | — | — | C | — | — | — |
| HPV18 | 43 | | — | — | — | — | C | G | G | G | — | — | — | — | — | — | — | — | — | — | — |
| HPV33 | 65 | | — | — | — | — | — | — | — | | — | — | — | — | — | — | — | — | — | — | — |

The URR/E6 positive strand primers are used as mixtures:
WD72 and WD73; WD72 and WD76; and WD72 and WD77.

E7 Consensus Negative Strand Primer

| | | | | | | | | | | | | | | | | | |
|---|---|---|---|---|---|---|---|---|---|---|---|---|---|---|---|---|---|
| WD70 | | 5' | G | C | R | C | A | G | A | T | G | G | G | R | C | A | C | A | C |
| WD71 | | 5' | G | C | A | C | A | C | C | A | C | G | G | A | C | A | C | A | C |
| HPV06 | 813 | 5' | G | C | G | C | A | G | A | T | G | G | G | A | C | A | C | A | C |
| HPV11 | 813 | | — | — | — | — | — | — | — | — | — | — | — | — | — | — | — | — | — |
| HPV16 | 845 | | — | A | A | — | — | — | — | — | — | — | — | G | — | — | — | — | — |

TABLE 6-continued

| | | | | | | | | | | | | | | | | | | | | | | |
|---|---|---|---|---|---|---|---|---|---|---|---|---|---|---|---|---|---|---|---|---|---|---|
| HPV18 | 894 | | — | — | A | — | — | C | C | A | C | — | — | — | — | — | — | — | — | — | — | |
| HPV33 | 856 | | — | — | A | — | — | — | G | — | A | — | — | G | — | — | — | — | — | — | |
| WD68 | | 5' | C | A | C | A | C | A | A | T | D | Y | Y | Y | A | G | T | G | T | G | C | C | C |
| WD69 | | 5' | C | A | C | A | C | A | A | A | G | G | A | C | A | G | G | G | T | G | T | T | C |
| HPV06 | 801 | 5' | C | A | C | A | C | T | A | T | G | T | T | T | A | G | T | G | T | T | C | C | C |
| HPV11 | 801 | | — | — | — | — | — | A | — | — | A | — | — | — | — | — | — | — | G | — | — | — | |
| HPV16 | 833 | | — | — | — | — | — | A | — | — | T | C | C | — | — | — | — | — | G | — | — | — | |
| HPV18 | 882 | | — | — | — | — | — | A | — | A | — | G | A | C | — | — | G | — | — | G | T | T | — |
| HPV33 | 844 | | — | — | — | — | — | A | — | — | C | — | C | — | — | G | — | — | — | | | | |

The E7 negative strand primers are used as mixtures: WD70 and WD71; and WD68 and WD69.

E6 Consensus Negative Strand Primer

| | | | | | | | | | | | | | | | | | | | |
|---|---|---|---|---|---|---|---|---|---|---|---|---|---|---|---|---|---|---|---|
| WD67 | | W | G | C | A | W | A | T | G | G | A | W | W | G | C | Y | G | T | C | T | C |
| WD66 | | A | G | C | A | T | G | C | G | G | T | A | T | A | C | T | G | T | C | T | C |
| WD154 | | T | C | C | G | T | G | T | G | G | T | G | T | G | T | C | G | T | C | C | C |
| WD155 | | W | S | C | A | W | A | T | G | G | W | W | W | G | Y | C | G | T | C | Y | C |
| WD163 | | W | G | C | A | W | A | T | G | G | A | W | W | G | Y | Y | G | T | C | Y | C |
| WD164 | | W | S | C | A | W | A | T | G | G | W | D | W | G | Y | Y | G | T | C | Y | C |
| HPV6 | 286 | T | G | C | A | T | A | T | G | G | A | T | A | G | C | C | G | C | C | T | C |
| HPV11 | 286 | — | — | — | — | A | — | G | — | — | — | A | — | — | T | T | — | T | — | — | — |
| HPV16 | 286 | A | — | — | — | — | — | — | — | — | — | T | C | — | — | — | A | T | — | — | — |
| HPV18 | 292 | A | — | — | — | — | — | G | C | — | — | — | T | A | T | A | — | T | — | — | — |
| HPV31 | | — | C | — | G | — | G | — | — | — | — | T | G | T | — | T | — | — | T | — | C | — |
| HPV33 | 390 | — | C | — | — | A | — | — | — | — | — | — | T | T | — | — | C | T | — | — | — |

Additional E6 consensus negative strand primers located in a different region of the gene, are used in pairs as shown below. The three primer sets shown, WD157 and WD160; WD158 and WD161; and WD159 and WD162, each correspond to the same genomic HPV region, but they differ in length. Primers WD160, WD161, WD162 are HPV18 specific.

E6 consensus probes can also be used as E6 consensus positive strand primers. When used as E6 consensus primers, the E6 consensus probes are used in the following combinations: WD65 and WD64; WD83 and WD64; and WD84 and WD64. The E6 consensus probes are depicted in Table 7.

TABLE 7

| | | | | | | | | | | | | | | | | | |
|---|---|---|---|---|---|---|---|---|---|---|---|---|---|---|---|---|---|
| E6 Consensus Probes | | | | | | | | | | | | | | | | | |
| WD65 | | M | G | A | G | A | C | R | G | C | W | W | T | C | C | A | T | W | T | G |
| WD83 | | M | G | A | G | A | C | R | G | S | W | W | T | C | C | A | T | W | T | G |
| WD84 | | M | G | A | G | A | C | R | G | V | W | W | T | C | C | A | T | W | T | G |
| WD64 | | A | G | A | G | A | C | A | G | T | A | T | A | C | C | G | C | A | T | G |
| HPV6 | 267 | C | G | A | G | G | C | G | G | C | T | A | T | C | C | A | T | A | T | G |
| HPV11 | 267 | — | — | — | — | A | — | A | A | — | — | T | — | — | — | C | — | T | — | — |
| HPV16 | 266 | A | — | — | — | A | T | — | — | G | A | — | — | — | — | — | — | — | — | — |
| HPV18 | 273 | A | — | — | A | — | A | — | T | A | T | A | — | — | G | C | — | — | | |
| HPV33 | 271 | A | — | — | — | A | G | — | — | A | A | — | — | — | — | — | — | T | — | — |
| WD134 | | G | A | G | G | T | A | T | W | T | G | A | H | T | T | T | G | C | | |
| WD135 | | G | A | G | A | T | W | T | A | T | K | C | A | T | A | T | G | C | | |

To determine the type of the HPV present in a sample

| | |
|---|---|
| WD157 | TTCTAMTGTWGTTSCATAYACASHATA |
| WD160 | CCAATGTGTGTCTCCATACACAGAGTC |
| WD158 | CTAMTGTWGTTSCATAYACASHATA |
| WD161 | AATGTGTGTCTCCATACACAGAGTC |
| WD159 | TAMTGTWGTTSCATAYACASHATA |
| WD162 | ATGTGTGTCTCCATACACAGAGTC |

Predicted Sizes of Products from E6 Consensus Primers

| | | Product Size for HPV Type | | | | |
|---|---|---|---|---|---|---|
| URR/E6 Primer | E7 Primer | HPV6 | HPV11 | HPV16 | HPV18 | HPV33 |
| WD72 and WD73 | WD70 and WD71 | 770 | 770 | 802 | 844 | 791 |
| WD72 and WD76 | WD70 and WD71 | 770 | 770 | 802 | 844 | 791 |
| WD72 and WD77 | WD70 and WD71 | 770 | 770 | 802 | 844 | 791 |
| WD72 and WD73 | WD68 and WD69 | 758 | 758 | 790 | 832 | 779 |
| WD72 and WD76 | WD68 and WD69 | 758 | 758 | 790 | 832 | 779 |
| WD72 and WD77 | WD68 and WD69 | 758 | 758 | 790 | 832 | 779 |
| WD72 and WD73 | WD66 and WD67 | 243 | 243 | 242 | 242 | 225 |
| WD72 and WD76 | WD66 and WD67 | 243 | 243 | 242 | 242 | 225 |
| WD72 and WD77 | WD66 and WD67 | 243 | 243 | 242 | 242 | 225 |

Those skilled in the art will recognize that the E6 consensus primers of the invention amplify a sequence that comprises a portion of E7 DNA. To determine if amplification has occurred when the E6 consensus primers are used in the method of the invention, E6 consensus probes are provided. E6 consensus probes WD134 and WD135 are directed to the small E6 amplification product and are used together as a mixture. The when the E6 consensus primers are used in the method of the invention, E6 type-specific probes are provided. These probes are depicted in Table 8. Using URR/E6 consensus primers comprising positive strand primers of Table 6 with WD70 and WD71 or WD68 and WD69 any of the HPV typing probes of Table 8 or Table 8A will be effective. These typing probes are also useful when E1 negative strand primers are used for amplification with the URR/E6 positive strand consensus primers.

both TYP02 and TYP01 and can be omitted from the amplification. The E1 region is highly conserved among HPVs, however, and although typing of the sample is possible with an E1 amplification, typing is

TABLE 8

| HPV Typing Probes for Use with E6 Amplified Sequences | | | |
|---|---|---|---|
| Probe | Specificity | Sequence | Genome Position |
| WD78 | HPV6 | 5' CGAAGTGGACGGACAAGAT | 643 |
| WD79 | HPV11 | 5' CAAGGTGGACAAACAAGACG | 643 |
| WD80 | HPV16 | 5' GAACACGTAGAGAAACCCAG | 534 |
| WD81 | HPV18 | 5' CAACCGAGCACGACAGGA | 530 |
| WD82 | HPV33 | 5' GAGGTCCCGACGTAGAGAA | 534 |

TABLE 8A

| HPV Typing Probes for Use with Small E6 Amplified Sequences | | | |
|---|---|---|---|
| Probe | Specificity | Sequence | Genome Position |
| WD165 | HPV31 | 5' AAATCCTGCAGAAAGACCTC | |
| WD166 | HPV31 | 5' CCTACAGACGCCATGTTCA | |
| WD167 | HPV39 | 5' CCTTGCAGGACATTACAATAG | |
| WD168 | HPV39 | 5' CAGACGACCACTACAGCAA | |
| WD169 | HPV42 | 5' GGTGCAAAAAGCATTAACAG | |
| WD102 | HPV18 | 5' ACAGTATTGGAACTTACAG | 213 |
| WD103 | HPV16 | 5' CAACAGTTACTGCGACG | 206 |
| WD104 | HPV33 | 5' GCAGTAAGGTACTGCAC | 88 |
| WD132 | HPV18 | 5' GACAGTATTGGAACTTACAG | 213 |
| WD133 | HPV6 | 5' ACACCTAAAGGTCCTGTTTC | 248 |
| WD134 | HPV11 | 5' ACACTCTGCAAATTCAGTGC | 175 |

The typing probes of Table 8A are useful with the positive strand URR/E6 consensus primers selected from WD76, WD66 and WD154; WD157 and WD160; WD158 and WD161; WD159 and WD162; WD66 and WD155; WD66 and WD163; and WD66 and WD164. These primers produce a small E6 amplification product of approximately 250 base pairs in length.

The present invention also provides primers that are complementary to sequences in the HPV E1 region. These E1 primers can be used to amplify only E1 region sequences or can be used in conjunction with E6/E7 primers to amplify seqences from E6, E7, E1, and combinations of these three regions. These E1 primers are shown below in Table 9.

more readily accomplished when the E1 primers are used in conjunction with E6 or E7 primers as follows. For instance, one can amplify the E6/E7 region using the following E1 and E6/E7 primer pairs: (1) WD72, WD76 and TYN01, TYN02, TYN03; (2) WD64, WD65 and TYN01, TYN02, TYN03; (3) WD72, WD76 and TYN04, TYN05, TYN06; (4) WD64, WD65 and TYN04, TYN05, TYN06; (5) WD72, WD76 and TYN07, TYN08; and (6) WD64, WD65 and TYN07, TYN08. In these latter amplifications the entire E7 region is amplified. Thus, these amplifiction products can be detected with the E7 consensus probed depicted below:

| TYP09 | 5' | G | A | G | C | A | A | T | T | A | G | W | A | G | A | C |
|---|---|---|---|---|---|---|---|---|---|---|---|---|---|---|---|---|
| TYP12 | | — | — | — | — | — | — | — | — | — | A | R | Y | — | — | — |

Those skilled in the art recognize that the specific

TABLE 9

| E1 POSITIVE STRAND PRIMERS | | | | | | | | | | | | | | | | | | | |
|---|---|---|---|---|---|---|---|---|---|---|---|---|---|---|---|---|---|---|---|
| TYP01 | 20MER | A | T | G | G | C | K | G | A | Y | C | C | T | G | M | A | G | G | T | A | C |
| TYP02 | 20MER | — | — | — | — | — | — | — | — | — | G | A | T | T | C | — | — | — | — | — | — |
| TYP03 | 20MER | — | — | — | — | — | — | — | — | — | C | C | T | T | C | — | — | — | — | — | — |
| TYP04 | 20MER | T | G | T | A | M | W | G | G | M | T | G | G | T | T | T | T | A | T | G | T |
| TYP05 | 20MER | — | — | — | — | — | — | — | — | — | — | — | — | — | — | — | G | A | G | — | — |
| TYP06 | 20MER | — | — | — | — | — | — | — | — | — | — | — | — | — | — | — | A | T | G | — | — |
| E1 NEGATIVE STRAND PRIMERS | | | | | | | | | | | | | | | | | | | |
| TYN01 | 20MER | G | T | A | C | C | T | K | C | A | G | G | R | T | C | M | G | C | C | A | T |
| TYN02 | 20MER | — | — | — | — | — | — | G | A | A | T | C | — | — | — | — | — | — | — | — | — |
| TYN03 | 20MER | — | — | — | — | — | — | G | A | A | G | G | — | — | — | — | — | — | — | — | — |
| TYN04 | 20MER | A | C | A | T | A | A | A | A | C | C | A | K | C | C | W | K | T | A | C | A |
| TYN05 | 20MER | — | — | C | T | C | — | — | — | — | — | — | — | — | — | — | — | — | — | — | — |
| TYN06 | 20MER | — | — | C | A | T | — | — | — | — | — | — | — | — | — | — | — | — | — | — | — |
| TYN07 | 20MER | T | C | C | A | C | T | T | C | A | G | W | A | T | T | G | C | C | A | T | A |
| TYN08 | 20MER | — | — | — | — | — | — | — | — | — | — | — | Y | A | — | — | — | — | — | — | — |

These E1 primers can be used in a variety of embodiments of the present invention. For instance, amplifications wholly within the E1 region can be performed using the primer pairs: (1) TYP01, TYP02, TYP03, and TYN07, TYN08; or (2) TYP04, TYP05, TYP06 and TYN07, and TYN08. Note that TYP03 is similar to primers and probes disclosed herein are merely illustrative of the invention. For instance, because the primers and probes of the invention are single-stranded DNA molecules, and because the target DNA (HPV DNA in a sample) is double-stranded DNA, useful primers and probes of the invention can be constructed merely by synthesizing primers and probes complementary to those specifically disclosed herein. The primers and probes of the invention can also be prepared to amplify and detect sequence variations within areas of HPV genomes other than those specifically exemplified herein.

Primers of the invention are generally 18 to 21 nucleotides in length and are designed to have a high degree of homology with HPV sequences. For instance, in the design of the genital HPV consensus primers of the invention, a high degree of homology with all five major genital HPVs (HPV types 6, 11, 16, 18, and 33) was required. For each region to be amplified, two regions of homology are required, one for negative-strand primers and another for positive-strand primers. To identify a homology region, viral sequences are compared. Once a homology region is identified, a consensus primer is designed. Degenerate bases can be used in the design to accommodate positions at which an individual virus varies in sequence from the homology sequence. As many degenerate positions are made as is necessary so that all viral sequences have fewer than three mismatches with the consensus primer. The degenerate positions are chosen so that the smallest number of degenerate bases accommodates the largest possible number of viral sequences.

If a particular viral sequence has a large number of mismatches with the consensus sequence, then a type-specific primer is made for that virus. The type-specific primer is mixed with the degenerate primer that was designed for other viruses to make the consensus primer. Any mismatches that are not accommodated by the degenerate positions in the primer should generally be located more than 3 bases from the 3' end of the primer. Likewise, any degenerate positions should be more than 3 bases from the 3' end of the primer.

Estimated minimum and maximum $T_m$s for a degenerate primer should be between 54 and 64 degrees C. $T_m$s are estimated by the non-empirical formula: each G or C contributes 4 degrees C to the $T_m$; each A or T contributes 2 degrees C to the $T_m$; and the $T_m$ is the sum of the calculated values. Finally, primers should not be designed to span palindromes or repetitive sequences.

Consensus probe design is similar to consensus primer design, except that consensus probes generally do not contain as many mismatches as consensus primers. As a result, the $T_m$ for a probe can be higher than the $T_m$ for a primer. However, where a mismatch or degenerate position occurs with respect to the 3' end is not as critical for consensus probes as it is for consensus primers.

Type-specific probes are designed so that a given probe will generally have less than 75% similarity with sequences from HPV types distinct from that recognized by the probe. The type-specific probes are usually 18–20 nucleotides in length with estimated $T_m$s in the range of 58 to 64 degrees C.

Those skilled in the art also recognize from the present disclosure that the method of the present invention can be carried out in a variety of ways. The present method is applicable to any human papillomavirus and especially preferred for detecting and typing genital HPVs. The method can be used to detect isolate-to-isolate variation within a particular HPV type and can also be used to screen for significant changes in the HPVs present in a patient. In one embodiment of the invention, consensus primers to more than one region of HPV DNA will be used, ensuring that if any portion of the HPV genome has been deleted, other regions can still be detected. In a similar fashion, the typing of the amplified DNA can be done using a variety of type-specific probes that recognize different regions of the amplified DNA.

Those skilled in the art recognize that the present invention can also be used to detect HPV mRNA present in a sample. The expression of certain HPV mRNA species, particularly E6 and E7 mRNAs, may be indicative of the likelihood than an HPV infection will progress to carcinoma. To detect an HPV mRNA by the method of the present invention, the mRNA can be treated with reverse transcriptase in an appropriate reaction mixture to synthesize a cDNA molecule. The primer used in the reverse transcription reaction can be a consensus primer of the invention or can be a different oligonucleotide that hybridizes near the 3' end of the mRNA. This cDNA copy is then made into a double stranded DNA molecule, which can be detected and typed in accordance with the method of the present invention.

The consensus primers of the present invention can also be used to detect HPV types previously uncharacterized. For instance, HPV isolates 36 and 88, noted in Table 4, above, have never before been characterized. Thus, the consensus primers of the invention can be used to amplify DNA sequences of previously unknown HPV types. The amplified DNA can then be sequenced and the sequence data used to generate type-specific probes for use in the method of the present invention.

The examples provided below merely illustrate the invention and in no way limit the scope of the accompanying claims.

EXAMPLE 1

Preparation of Clinical Samples for Amplification by the Polymerase Chain Reaction Cervical and vulvar swabs and penile scrapes typically contain $10^3$–$10^5$ cells. Cells were suspended in 2 ml of phosphate-buffered saline, pelleted by centrifugation, and the supernatant discarded. If cell suspensions were to be stored for a period of time before the test, antibiotics were generally added to the suspension (a commercially available antibiotic, such as 2×Fungi Bact Solution, is suitable for this purpose). The cell number was estimated, and if blood was present in the sample, the cells were suspended in 1 ml of TE buffer (10 mM Tris-HCl, pH 7.5, and 1 mM EDTA) to lyse the red blood cells and then repelleted. About $10^2$–$10^4$ cells were used per PCR reaction. The cells were first suspended in 100 $\mu$l of buffer containing 50 mM Tris, pH 8.5; 1 mM EDTA; 1% Laureth-12; and 200 $\mu$g/ml proteinase K. This mixture was incubated at 55 degrees C. for about 1 hour, and then the proteinase K was heat-inactivated by incubating the mixture at 95 degrees C. for 10 minutes. The samples were then treated in accordance with a standard PCR protocol with the consensus primers of the invention to amplify any HPV sequences present. Aliquots containing $10^2$–$10^4$ cells were used per 100 $\mu$l of PCR reaction mixture.

Another method for preparing a cell suspension for PCR involves suspending the cells in 100 $\mu$l of deionized water and incubating the resulting suspension at 100 degrees C. for 10–15 minutes.

EXAMPLE 2

Extraction of Tissue from Paraffin

The method of the present invention will often be used to determine whether tissue sections in paraffin contain HPV. To prepare such a tissue section, typically 5-10 μM in width, for use in the present method, the following procedure was employed.

The tissue section was extracted twice with 1 ml of xylene or an alkane such as octane to remove the paraffin. Each extraction was for about one-half hour. The tissue section was then rinsed twice with 100% ethanol to remove the extracting agent and dried in a rotary evaporator. The section was then suspended in Taq buffer with detergents and proteinase K and treated as described in Example 1, except that the 55° C. incubation was for 2-4 hours.

After heat inactivation of the proteinase K, the suspension was centrifuged to pellet debris, and about 1-20 μl of the supernatant were used for each PCR reaction.

EXAMPLE 3

PCR PROTOCOLS

All PCR protocols were carried out using a Perkin-Elmer/Cetus Instruments Thermal Cycler instrument. A typical reaction mixture contained 50 pmoles of consensus positive-strand primer; 50 pmoles of consensus negative-strand primer; 2.5 Units of Taq polymerase; 10 μl of 10×PCR buffer (0.5M KCl; 100 mM Tris, pH=8.5; 20-40 mM $MgCl_2$; 0.2 mM of each dNTP; about 10 μl of a clinical or paraffin sample; and deionized water to 100 μl.

PCR reaction times for use with clinical samples were as follows. The machine was heated to 72 degrees C. before the samples were placed into the machine. The machine was then programmed to execute the following temperature changes: thirty cycles of 30 seconds at 95 degrees C., 30 seconds at 55 degrees C. and 60 seconds at 72 degrees C.; 5 minutes at 72 degrees C.; and then hold at 15 degrees C.

For paraffin sections, the machine was programmed to execute temperature changes as follows: forty cycles of 50 seconds at 95 degrees C., 50 seconds at 55 degrees C., and 2 minutes at 72 degrees C.; 5 minutes at 72 degrees C.; and then hold at 15 degrees C.

If the PCR product was expected to be longer than 600 bp, the machine was programmed to execute temperature changes as follows: 1 minute at 72 degrees C.; forty cycles of a 50 second ramp to 95 degrees C., 20 seconds at 95 degrees C., a 90 second ramp to 55 degrees C., 30 seconds at 55 degrees C., a 50 second ramp to 72 degrees C., and 3 minutes at 72 degrees C.; 5 minutes at 72 degrees C.; and then hold at 15 degrees C.

To determine by use of consensus probes if amplification had occurred, about 10 μl of the reaction mixture were added to 140 μl of deionized water and 50 μl of 4×denaturing solution (1.6M NaOH and 100 mM EDTA). About 100 μl of this denatured solution were spotted onto a positively-charged, nylon Genetrans membrane using a BioRad dot-blot appartus. The resulting dot was rinsed once with 200 μl of 20XSSC. The membrane was then removed from the blotter, air-dried, and exposed to ultraviolet light (with the DNA facing the light) to covalently attach the DNA to the membrane.

The membrane was pre-hybridized at least 45 minutes at 68 degrees C. in a water bath. The pre-hybridization solution contained 6XSSC, 5×Denhardt's solution, and 0.5% SDS. Alternatively, the membranes can merely be rinsed with pre-hybridization solution. The pre-hybridization solution was decanted. About 10 ml of the pre-hybridization solution were added to 100 μl of 10 mg/ml denatured salmon sperm DNA and to about $1\times10^6$ Cherenkov counts per mL of consensus probe (0.2 pmole). This solution was added back to the membrane, and the consensus probe was allowed to hybridize at 55 degrees C. for at least 1 hour. After the hybridization, the hybridization mix was decanted and the membrane was quickly rinsed in a 30-55 degree C. wash to remove excess probe. The wash solution was composed of 2XSSC and 0.1% SDS. The membrane was then washed in fresh wash solution heated to 55 degrees C. For this wash step the membrane was placed in a tray containing heated wash solution and the tray was placed in a 55 degrees C. water bath for 10 minutes. This wash procedure was repeated once, and then the membrane was rinsed with a solution of 2XSSC and 0.1% SDS heated to 55 to 60 degrees C. An alternative wash procedure involves the same methodology but wash solutions at different temperatures, i.e., a 55 degrees C. wash solution in the first two washes and a room temperature wash solution in the final rinse. The membrane was then air-dried and allowed to expose X-ray from 7 to 48 hours.

To determine the HPV type of amplified DNA, PCR reaction mixtures were hybridized to type-specific probes as described above. The only significant difference in the procedure was that the final wash of the filter was done at a temperature very near the Tm of the particular type-specific probe. Filters hybridized to different type-specific probes were not washed together.

Other modifications of the embodiments of the invention described above that are obvious to those of ordinary skill in the areas of molecular biology, medical diagnostic technology, biochemistry, virology, genetics and related disciplines are intended to be within the scope of the accompanying claims.

We claim:

1. A method for detecting genital human papillomavirus (HPV) in a sample and typing the HPV, if present, comprising:

(a) treating the sample with a pair of consensus HPV primers, DNA polymerase, and deoxynucleoside 5'-triphosphates under conditions such that an extension product of a consensus primer can be synthesized if HPV is present, wherein said consensus primers are a mixture of oligonucleotides that comprises at least a pair of primers sufficiently complementary to separate strands of HPV DNA to hybridize thereto so that the extension product synthesized from one member of said pair, when separated from its complementary strand, can serve as a template for synthesis of the extension product of the other member of said pair, said pairs of consensus primers selected from the group consisting of (a) FS10, JS15 and JS16; (b) FS17, JS15 and JS16; and (c) MY01, JS15 and JS16;

(b) separating the primer extension products, if present, from the templates on which the extension products were synthesized to form single-stranded molecules;

(c) treating the single-stranded molecules generated in step (b), if any, with the consensus primers of step (a) under conditions such that a primer extension product is synthesized using each of the single-stranded molecules produced in step (b) as a template;

(d) repeating steps (b) and (c) at least once;
(e) determining of amplification has occurred; and, if amplification has occurred,
(f) hybridizing a type-specific DNA probe to said amplified DNA; and
(g) determining if hybridization has occurred.

2. The method of claim 1, wherein step (e) comprises treating the reaction mixture prepared in step (d) under hybridizing conditions with a consensus probe and determining if hybridization has occurred.

3. The method of claim 1, wherein said primers are selected from the group consisting of FS10, JS15, JS16, and FS17.

4. The method of claim 2, wherein said consensus probe is FS10.

5. Oligonucleotides useful for detecting HPV DNA in a sample selected from the group consisting of: FS10, JS15, JS16, and FS17.

6. A composition of claim 5 wherein the composition comprises a mixture of primer pairs, said pairs consisting of: (a) FS10, JS15 and JS16; (b) FS17, JS15 and JS16; and (c) MY01, JS15 and JS16.

* * * * *